United States Patent [19]

Conrad et al.

[11] 4,084,277
[45] * Apr. 18, 1978

[54] COLLAPSIBLE GUARD RAIL

[76] Inventors: Raymond M. Conrad, 745 Woodruff Rd., Milford, Conn. 06460; Charles R. Whitcomb, Rowley Rd., Woodbury, Conn. 06798

[*] Notice: The portion of the term of this patent subsequent to Aug. 31, 1993, has been disclaimed.

[21] Appl. No.: 727,267

[22] Filed: Sep. 27, 1976

Related U.S. Application Data

[62] Division of Ser. No. 537,683, Dec. 30, 1974, Pat. No. 3,997,792.

[51] Int. Cl.² ........................ A47D 7/02; A47C 21/00
[52] U.S. Cl. ............................................ 5/331; 5/100
[58] Field of Search ..................... 5/92, 100, 114, 331; 256/59, 65; 248/226 B; 297/417; 52/183; 269/322, 323, 328

[56] References Cited

U.S. PATENT DOCUMENTS

| | | | |
|---|---|---|---|
| 2,136,088 | 11/1938 | Stevens | 5/331 |
| 3,093,839 | 6/1963 | Higgins | 5/331 |
| 3,401,918 | 9/1968 | Wiese | 256/59 |
| 3,463,457 | 8/1969 | Alexander | 256/59 |
| 3,930,273 | 1/1976 | Stern | 5/331 |

*Primary Examiner*—Casmir A. Nunberg
*Attorney, Agent, or Firm*—McCormick, Paulding & Huber

[57] ABSTRACT

An X-ray table has a cassette holder for receiving an X-ray film cassette and releasably retaining it generally adjacent the lower surface of the table top and at least one collapsible guard rail assembly supported for movement between raised and lowered positions. The guard rail assembly includes a hollow elongated top rail supported above the plane of the table top in said raised position and disposed adjacent an associated side edge of the table top immediately above the cassette holder in said lowered position. The support members which carry each top rail and the means for retaining it in its raised position are substantially wholly disposed within the confines of the hollow top rail in its lowered or collapsed position.

10 Claims, 7 Drawing Figures

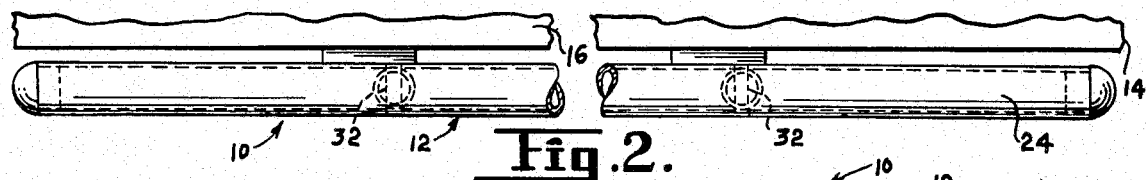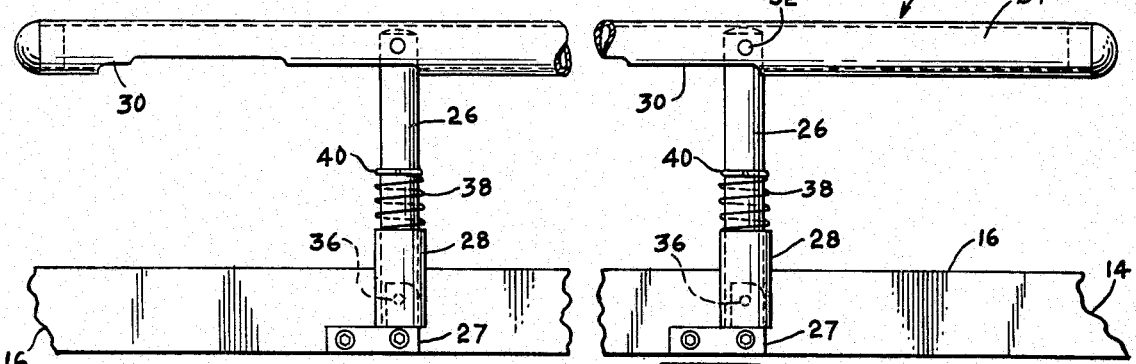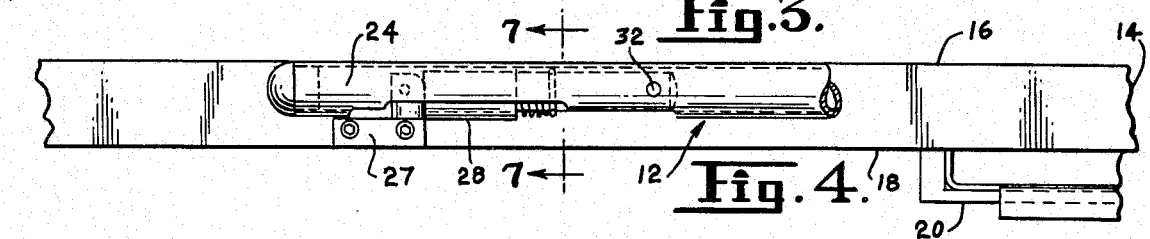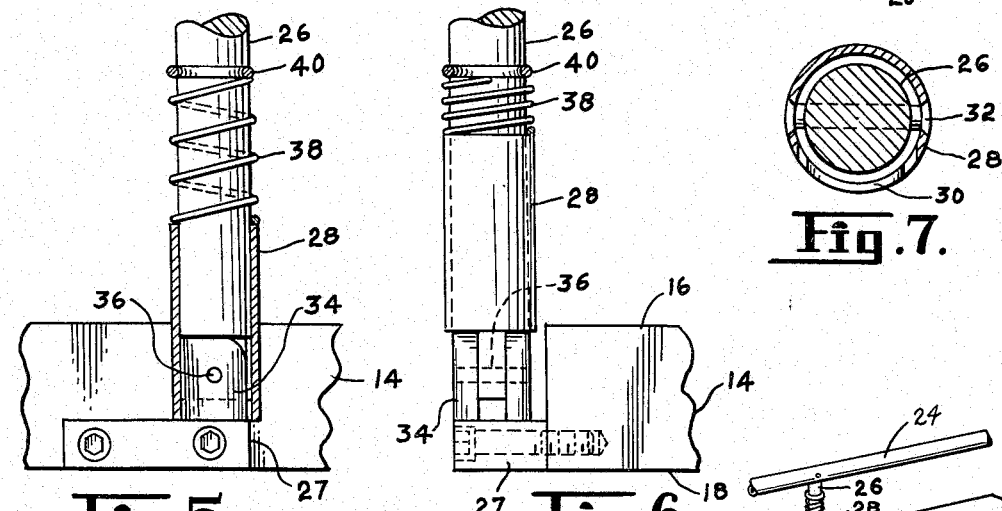

COLLAPSIBLE GUARD RAIL

This is a division of application Ser. No. 537,683, filed Dec. 30, 1974 now U.S. Pat. No. 3,997,792.

BACKGROUND OF THE INVENTION

This invention relates to a collapsible guard rail assembly and an improved X-ray table which includes such guard rail structure.

In a hospital emergency radiological facility it is frequently necessary to take X-ray photographs of patients who may be in unconscious or semi-conscious state or whose motor control functions may be otherwise impaired by injury. Generally, the patient must remain unattended on the X-ray table while the radiologist operates the X-ray equipment from a remote location as, for example, from behind radiation barrier. Some form of safety device is generally required to prevent the patient from falling from the table while the X-ray photographs are being taken. Heretofore, various restraining devices have been employed to immobilize the patient or secure him to the table. However, such restraining devices are not wholly satisfactory, because of time required to apply and remove them. Such restraining devices may, under some circumstances, cause injury to the patient or impair the function of the X-ray equipment. Guard rails have not gained general acceptance for use on radiological equipment. It is essential that a guard rail for use on an X-ray table not interfere with movement of a patient onto or from the table or constitute a potential source of injury to the patient during such movement. It is further essential that such a guard rail in no way interfere with rapid manipulation of film cassettes during the loading and unloading of the cassette holder. Guard rails heretofore available have failed to fully satisfy the aforesaid requirements. The present invention is concerned with the aforesaid problems.

SUMMARY OF THE INVENTION

In accordance with the invention an improved collapsible guard rail assembly is provided which includes means for mounting the guard rail assembly on a table such as an X-ray table; a top rail, means supporting the top rail on the mounting means for movement between raised and lowered positions relative to the table, and means for releasably retaining the top rail in its raised position. The supporting means and the releasable retaining means are substantially wholly disposed within the confines of the hollow top rail when it is in its lowered or collapsed position so that the top rail presents a low profile generally adjacent one edge of the table. An X-ray film cassette associated with the table and loaded from a position proximate the top rail in its lowered position is accessible in all positions of the top rail to permit loading and unloading of film cassettes.

BRIEF DESCRIPTION OF THE DRAWING

FIG. 1 is a fragmentary perspective view of an X-ray table having collapsible guard rail assemblies and embodying the present invention.

FIG. 2 is a somewhat enlarged fragmentary plan view of the X-ray table of FIG. 1.

FIG. 3 is a somewhat enlarged fragmentary side elevational view of the X-ray table of FIG. 1 and shows the guard rails in raised position.

FIG. 4 is similar to FIG. 3 but shows the guard rail in its lowered or collapsed position.

FIG. 5 is a somewhat further enlarged fragmentary side elevational view of the X-ray table of FIG. 1 and shows a guard rail in raised position and partial vertical section.

FIG. 6 is a fragmentary right end elevational view of the X-ray table of FIG. 1.

FIG. 7 is a somewhat enlarged fragmentary sectional view taken along the line 7—7 of FIG. 4.

DETAILED DESCRIPTION OF PREFERRED EMBODIMENT

Turning now to the drawing and referring first particularly to FIGS. 1-3, an X-ray table embodying the invention and indicated generally by the reference numeral 10 has a pair of collapsible guard rail assemblies indicated generally at 12, 12 mounted thereon. The X-ray table 10 includes a table top 14 which has upper and lower surfaces respectively indicated at 16 and 18 and is supported on a base (not shown) for pivotal adjustment between horizontal and vertical positions as indicated by the direction arrow 19 in FIG. 1. However, for convenience, the table 10 is described and claimed in its horizontal position, as it appears oriented in the drawing. A drawer-like film cassette retainer 20 mounted on the table 10 below the table top 14 opens toward at least one side edge thereof and is movable with and longitudinally relative to the table top 14. The cassette retainer 20 releasably retains a film cassette 22 in a predetermined position relative to the upper surface 16 and generally adjacent relation to the lower surface 18.

A typical collapsible guard rail assembly 12 comprises an elongated hollow top rail 24 carried by a plurality of support members 26, 26 attached to mounting members 27, 27 which are secured to one edge of the table top 14 by suitable fasteners, substantially as shown. The guard rail 24 is supported for movement with the table top 14 and for pivotal movement relative thereto about an axes extending transversely of the table 10 between a raised or active position shown in FIGS. 1 and 3 and a lowered or inactive position illustrated in FIG. 4. At least one retaining member or collar 28 associated with one of the support members 26 releasably retains the guard rail assembly 12 in its raised position, as will be hereinafter further discussed. In accordance with the present invention, when the guard rail assembly 12 is in its lowered or collapsed position, the support members 26, 26 and the retaining member 28 are substantially wholly disposed within the confines of the hollow top rail 24. In the latter position the top rail 24 is disposed generally adjacent an associated side edge of the table top 14 and presents a substantially smooth low profile. It will be noted that when the guard rail assembly 12 is in its inactive or collapsed position (FIG. 4) at least a portion of each mounting bracket 27 is also disposed within the confines of the hollow top rail 24. The film cassette 22 may be loaded into or removed from the cassette retainer 20 when the guard rail assembly 12 is in either of its positions.

Considering now a typical guard rail assembly 12 in further detail, the top rail 24 comprises an elongated generally cylindrical tube which has smooth, rounded end plugs in its opposite ends. At least one longitudinally extending slot opens through the lower surface of the rail 24, but preferably and as shown, a plurality of slots 30, 30 are formed in the top rail, the number of slots being equal to the number of support members 26, 26 which carry the rail.

Each support member 26 comprises an elongated generally cylindrical member connected at its upper end to the top rail 24 by a pivot pin 32 within an associated slot 30 near one end thereof, as best shown in FIGS. 2 and 3. Each mounting backet 27 comprises a generally L-shaped bracket which has transversely spaced apart upwardly extending portions, 34, 34 which receive the lower end portion of an associated support member 26 therebetween. A pivot pin 36 connects the lower end of the support member 26 to an associated bracket 27 for pivotal movement about an axis which extends transversely of the table 10. Preferably, and as shown, each support member 26 has a retaining member 28 supported thereon. A typical retaining member 28 comprises a generally cylindrical tubular sleeve which surrounds the lower end portion of an associated support member 26 and is freely slidable movable thereon between a retaining position shown in FIG. 5 and a releasing position shown in FIG. 6. A compression spring 38 preferably surrounds the support member 26 and acts between the sleeve 28 and a spring retainer or O ring 40 received in an annular groove in the support member 26 above the sleeve 28. The springs 40, 40 bias the sleeves 28, 28 to retaining position when the guard rail is moved to its raised or active position.

The guard rail may be employed when the table is either horizontal or vertically oriented. When the table 10 is horizontally positioned the guard rail assemblies 12, 12 serve as safety barriers to prevent a patient from accidentally falling from the table. When the table 10 is in its horizontal position, it will be apparent that the sleeves 28, 28 are biased to retaining positions under the influence of gravity when the guard rail is raised to its active position. Thus, if the guard rail assembly 12 is to be used on a table or the like supported in a fixed horizontal position the biasing springs 38, 38 may be omitted and such construction is contemplated within the scope of the invention. The guard rails may also be employed when the table is tilted to its vertical position as when it is used in fluoroscopy. When the table 10 is tilted to its vertical position and the guard rail assemblies 12, 12 are extended to active position, the springs 38, 38 bias the sleeves 28, 28 to retaining position to releasably retain the guard rail assemblies in extended position. When the table is in the latter position and the patient is standing in front of it with his back resting against the table support surface the guard rails 24, 24 may be grasped by the patient to steady himself relative to the table.

We claim:

1. A collapsible guard rail assembly for a table or the like, said guard rail assembly comprising means for mounting said guard rail assembly on a table, a hollow elongated top rail, means for supporting said top rail on said mounting means for movement relative thereto between active and inactive positions, said top rail in its inactive position being supported generally adjacent said mounting means by said supporting means, said top rail in its active position being maintained in spaced relation to said mounting means by said supporting means, and means for releasably retaining said top rail in said active position, said supporting means, said retaining means and at least a portion of said mounting means being wholly disposed generally within the interior confines of said top rail when said top rail is in said inactive position.

2. A collapsible guard rail assembly as set forth in claim 1 wherein said supporting means comprises a plurality of elongated support members each of said support members having one of its end portions pivotally connected to said mounting means and the other of its end portions pivotally connected to said top rail within the interior confines of said top rail.

3. A collapsible guard rail assembly as set forth in claim 2 wherein said top rail has a plurality of slots opening through the lower surface thereof and equal in number to the number of said support members and said other end portion of each of said support members extends into said top rail through an associated one of said slots when said top rail is in its active position.

4. A collapsible guard rail assembly as set forth in claim 1 wherein said retaining means is carried by said supporting means and movable relative thereto between a retaining position and a releasing position and said retaining means cooperates with said supporting means and said mounting means in its retaining position to releasably retain said top rail in its active position.

5. A collapsible guard rail as set forth in claim 4 including means for biasing said retaining means toward its retaining position.

6. A collapsible guard rail as set forth in claim 4 wherein said supporting means comprises a plurality of elongated support members pivotally connected to said top rail and said mounting means and said retaining means comprises a sleeve slidably received on an associated one of said support members.

7. A collapsible guard rail assembly for mounting on a table and for pivotal movement between raised and lowered positions relative to the table, said guard rail assembly comprising a plurality of mounting brackets for attachment to the table in horizontally spaced relation to each other, a single tubular top rail having a fixed length, a plurality of elongated support members equal in number to said mounting brackets, each of said support members having one of its end portions pivotally connected to an associated one of said mounting brackets and the other of its end portions pivotally connected to said top rail within the interior confines of said top rail, each of said other end portions extending upwardly into said top rail through a longitudinally extending slot in said top rail when said guard rail assembly is in its raised position, a tubular retaining sleeve slidably received on an associated one of said support members and movably longitudinally thereof between releasing and retaining positions, said retaining sleeve in its retaining position surrounding associated portions of said one support member and its associated mounting bracket to releasably retain said guard rail assembly in its raised position, said support members and said brackets cooperating to maintain said top rail in a generally horizontally disposed position above the plane of the table surface when said guard rail assembly is in its raised position, said support members, said retaining sleeve and at least a portion of each of said mounting brackets being disposed wholly within the interior confines of said top rail when said guard rail assembly is in its lowered position.

8. A collapsible guard rail assembly as set forth in claim 7 wherein each of said mounting brackets has an upwardly extending portion and said retaining sleeve partially surrounds said upwardly extending portion of its associated mounting bracket in said retaining position.

9. A collapsible guard rail assembly as set forth in claim 7 including a spring received on said one support member and acting between said one support member and said retaining sleeve to normally bias said retaining sleeve toward its retaining position.

10. A collapsible guard rail assembly as set forth in claim 9 wherein said spring is wholly disposed within the interior confines of said top rail when said guard rail assembly is in its lowered position.

* * * * *